(12) United States Patent
Demotte et al.

(10) Patent No.: US 8,951,747 B2
(45) Date of Patent: Feb. 10, 2015

(54) METHOD FOR MODULATING ACTIVITY OF T LYMPHOCYTES

(75) Inventors: Nathalie Demotte, Chastre (BE); Pierre Van Der Bruggen, Chaumont-Gistoux (BE); Thierry Boon-Falleur, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 233 days.

(21) Appl. No.: 13/429,873

(22) Filed: Mar. 26, 2012

(65) Prior Publication Data

US 2012/0196363 A1 Aug. 2, 2012

Related U.S. Application Data

(62) Division of application No. 12/451,011, filed as application No. PCT/US2008/002774 on Mar. 3, 2008, now abandoned.

(60) Provisional application No. 60/926,265, filed on Apr. 26, 2007.

(51) Int. Cl.

| | | |
|---|---|---|
| *G01N 33/00* | (2006.01) | |
| *C12N 5/00* | (2006.01) | |
| *C12N 5/07* | (2010.01) | |
| *A61K 31/7016* | (2006.01) | |
| *A61K 31/4745* | (2006.01) | |
| *A61K 45/06* | (2006.01) | |
| *C07K 14/725* | (2006.01) | |
| *C07K 14/705* | (2006.01) | |
| *G01N 33/50* | (2006.01) | |
| *C12N 5/0783* | (2010.01) | |
| *C07K 16/28* | (2006.01) | |
| *A61K 39/00* | (2006.01) | |

(52) U.S. Cl.
CPC .......... *A61K 31/7016* (2013.01); *A61K 31/4745* (2013.01); *A61K 45/06* (2013.01); *C07K 14/7051* (2013.01); *C07K 14/70517* (2013.01); *G01N 33/505* (2013.01); *C12N 5/0636* (2013.01); *A61K 2039/5158* (2013.01); *C12N 2500/22* (2013.01); *C12N 2500/34* (2013.01); *C12N 2501/59* (2013.01); *C12N 2501/73* (2013.01)
USPC .......................................... 435/7.24; 435/375

(58) Field of Classification Search
None
See application file for complete search history.

(56) References Cited

FOREIGN PATENT DOCUMENTS

WO    WO 2005/037293 A1 *  4/2005

OTHER PUBLICATIONS

Fournier and Schirrmacher (Expert. Rev. Vaccines 8(1); 51-66, 2009).*
Schrieber et al (Seminar. Immunol. 22: 105-112, 2010).*
Klebanoff et al (Immunol. Rev. 2011, 239: 27-44).*
De St. Groth et al (Immunology and Cell Biology 2004, 82: 260-268).*

\* cited by examiner

*Primary Examiner* — Gerald R Ewoldt
*Assistant Examiner* — Marianne DiBrino
(74) *Attorney, Agent, or Firm* — Abelman, Frayne & Schwab

(57) ABSTRACT

The invention relates to methods and compositions which modulate T lymphocyte activity. It has been found that two, T lymphocyte receptors, especially TCR and CD8, are present at a distance from each other on T lymphocyte surfaces. Via use of modulators which change the distance between these receptors, the activity of the T lymphocyte is modulated.

14 Claims, No Drawings

METHOD FOR MODULATING ACTIVITY OF T LYMPHOCYTES

RELATED APPLICATIONS

This application is a divisional of application Ser. No. 12/451,011 filed Feb. 8, 2010, now abandoned which is a 371 of Application Serial No. PCT/US08/02774 filed Mar. 3, 2008, which claims priority from provisional Application Ser. No. 60/926,265 filed Apr. 26, 2007. All of these applications are incorporated by reference.

FIELD OF THE INVENTION

The invention relates to methods for modulating activity of T lymphocytes, such as CD8⁺ T lymphocytes, or "CD8TLs". More specifically, it relates to treating T lymphocytes with low or no T cell activity with one or more compounds which act to bring two components critical to T lymphocyte activity, the T cell receptor (TCR), and co-receptor CD8 in proximity to each other sufficient to increase or restore T lymphocyte activity.

BACKGROUND OF THE INVENTION

Study of the immune system has shown it to be an extremely complex one, requiring countless signals in order to function optimally. See, e.g., Janeway, *Quant. Biol.*, 54:1-4 (1989), Paul, ed., *Fundamental Immunology*, (4$^{th}$ ed., 1998), both of which are incorporated by reference herein.

An essential feature of an immune response are the interactions between T lymphocytes and antigen presenting cells ("APCs"). Many cohesive molecules that are found on T cells and APCs increase during an immune response. Increased levels of these molecules are believed to be key to the fact that activated APCs are more effective at stimulating antigen specific T cell proliferation, than are resting APCs.

It is thus not surprising that the T cell immune response is a complex process, involving cell interactions, including those between T cells and accessory cells, including APCs, and production of soluble immune mediators. This T cell response is regulated by various T-cell surface receptors, including, but not being limited to, the T-cell receptor complex, as well as other "accessory" surface molecules. Many of these accessory molecules are naturally occurring cell surface differentiation (CD) antigens defined by the reactivity of monoclonal antibodies on the surface of cells.

It is well established that, on CD8TLs, the TCR and CD8 molecules co-participate in the recognition of a complex formed by an antigenic peptide, and a class I major histocompatibility complex, or "MHC" molecule. In humans, these MHC molecules are known as "human leukocyte antigens" or "HLAs." When "HLA" is used herein, it is to be understood that it is representative of MHCs generally.

Details of the aforementioned interaction are well established. TCRs are dimers, with "α" and "β" chains, and are sometimes referred to as "TCRabs". These molecules interact with the peptide, and the surrounding grove of the MHC class I molecule, with a kD generally higher than 3 mM, in syngeneic responses. The CD8 molecule, also heterodimeric, and sometimes referred to as CD8αβ, contacts the αβ constant region of the MHC class I molecules, with a kD of approximately 100 mM. See, Arcaro, et al., *J. Exp. Med.*, 194:1485-1495 (2001); Holler, et al., *Immunity*, 18:225-264 (2003).

When complexes of TCR and CD8 form, the resulting complexes have affinities for the MHC-peptide complexes that are about ten-fold higher than the TCR alone. Holler, supra.

Structurally, CD8αβ molecules are located in lipid rafts, in association with intracellular tyrosine kinase p56$^{lck}$. Arcaro, et al., supra, Arcaro, et al., *J. Immunol.*, 165:2068-2076 (2000). TCRs are associated with CD3γ, δ, ϵ and ζ chains, and are not located in rafts, but TCR-CD3 complexes interact closely with CD8-p56$^{lck}$ complexes that are found in rafts, so as to induce signal transduction when binding to antigen. Doucey, et al., *Eur. J. Immunol.*, 31:1561-1570 (2001); Montixi, et al., *EMBO J.*, 17:5334-5348 (1998).

After the initial binding of CD8TLs to target cells, additional TCRs congregate at the contact region, referred to as the "immunological synapse." Synapses mature to form distinct patterns with TCR molecules located in the center and surrounded by LFA-1 adhesion molecules, which are in turn surrounded by CD45 molecules. Huppa, et al., *Nat. Rev. Immunol.*, 3:973-983 (2003); van der Merwe, et al., *Semin. Immunol.*, 12:5-21 (2000). Further, the microtubule organizing center, or "MTOC" moves to the synapse, directing release of lytic granules into target cells. Grakoui, et al., *Science*, 285:221-227 (1999); Stinchcombe, et al., *Immunity*, 15:751-761 (2001). During the process, TCR molecules in the synapse begin internalizing, resulting in a considerable decrease of TCRs on the cell surface; however, newly synthesized and recycled TCRs move to the cell surface, and the initial level of TCRs on cell surfaces is recovered, usually, within 24 hours of antigen presentation. Valitutti, et al., *Nature*, 375:148-151 (1995).

It is also well known that if CD8TLs are stimulated, e.g., weekly, with their target antigen in the presence of growth factors, they can be kept in culture for several months. It has been observed, however, that their cytolytic activity can diminish or be lost completely.

Demotte, et al., *Eur. J. Immunol.*, 32:1688-1697 (2002), the disclosure of which is incorporated by reference, observed that CD8⁺ T lymphocytes lose their specific cytolytic activity if, instead of being stimulated weekly with tumor cells, are stimulated with Epstein Barr Virus ("EBV") transformed B cells which present the relevant antigenic peptide. The loss of effector function is always associated with loss of labeling by HLA-peptide tetramers. While Demotte et al. were not able to identify the reason for this loss of activity, they did eliminate loss of TCR or CD8 expression as reasons.

Galectin-3 is a well known molecule. An exemplary, but by no means exhaustive listing of the literature on this molecule includes Dumic, et al., *Biophysica. Acta.*, 616-635 (2006), Demetriou, et al., *Nature*, 409:733-739 (2001), both incorporated by reference, which provide details on the structure of galectin-3, as well as a role in forming a lattice, with glycoproteins, leading to restriction in recruitment of TCRs to antigen presentation sites.

Also of interest are U.S. Pat. No. 6,680,306, describing how surgical procedures can be improved by administering a carbohydrate which selectively binds to a galectin, including galectin-3; U.S. Pat. No. 6,890,906, which discusses how the use of complex carbohydrate molecules which bind to galectins, including galectin-3, can control angiogenesis, and U.S. Pat. No. 6,770,622 which describes a role for galectin-3 in tumor metastasis, and describes a truncated galectin-3 molecule useful in treating metastasis. All of these patents are incorporated by reference herein.

Nothing in these references, however, points to or suggests that galectin-3 has a role in the immunological process known as anergy.

It has now been found that the diminishing or loss of T lymphocyte activity is associated with physical separation of TCR and CD8 molecules. It has also been found that both the proximity of TCR and CD8 and the activity of the T lymphocytes can be restored via treatment of the CD8TLs with appropriate molecules.

How this is accomplished will be seen from the disclosure which follows.

DETAILED DESCRIPTION OF THE INVENTION

Example 1

CD8TL clone A10 which was isolated from a patient who had been vaccinated with a recombinant poxvirus, ALVAC, containing the region coding for peptide EVDPIGHLY (SEQ ID NO: 1), which consists of amino acids 168-176 of MAGE-3. The peptide is presented by HLA-A1 molecules. The CD8TLs were isolated by ex vivo tetramer sorting as described in Godelaine, et al., *J. Immunol.*, 171:4893-4897 (2003)).

On day 0, samples of CD8TL clone A10 (a total of $3\times10^5$ cells) were cultured, in 24-well plates, in the presence of $1\times10^6$ irradiated, allogeneic Epstein-Barr virus immortalized B cells (EBV-B cells), which served as feeder cells, and were stimulated with $1\times10^5$ irradiated tumor cells, which had been incubated, previously for 1 hour at 37° C., with 1 µg/ml of peptide, and washed. The culture medium was IMDM supplemented with AAG, 10% heat inactivated autologous human serum, and 50 U/ml of IL-2.

Fourteen days after the stimulation, the CD8TLs were then stained with complexes of HLA-A0101 folded with SEQ ID NO: 1, prepared as described by Coulie, et al., *Proc. Natl. Acad. Sci. USA,* 98:10290-10295 (2001), incorporated by reference. The complexes were biotinylated and then labeled with phycoerythrin ("PE"), using known methods. Staining was accomplished by incubating CD8TLs, for 10 minutes, at room temperature, with 5 nM of tetramer, and then washing.

The cells were found to have strong, homogenous binding to the tetramer and this set of properties is referred to hereafter as tetramer$^{high}$. At that day, the CD8TLs were again stimulated under the conditions described supra. By the 4$^{th}$ day, a homogenous, approximately 10 fold decrease in tetramer staining was observed (the tetramer$^{low}$ phenotype). By 7 days, the CD8TLs had recovered part of the ability to bind tetramer, and had recovered it completely by day 14.

Example 2

To study the decrease in tetramer binding discussed supra, experiments were carried out to determine if decreased surface expression of one or both of TCRαβ or CD8αβ was involved. To test this, cells were incubated with an anti-CD3.APC fluorescent antibody to identify T cells, washed, and then incubated for 15 minutes at 4° C. with 1/30 of anti-CD8.FITC, after which they were analyzed via FACS. To study TCRβ expression, cells were incubated with an anti-CD3APC antibody to identify T cells, washed, and then incubated for 15 minutes at 4° C. with TCRβ.FITC, then washed and fixed with 1% paraformaldehyde in PBS. The levels of surface expression of TCRβ, CD8α, CD8β, and TCRα on days 4 and 7 were the same as those observed on day 0.

Example 3

In addition to the experiments set forth, supra the effector capability of the T lymphocytes was tested, at various points during the period in which they were stimulated. Stimulation conditions are set forth in Example 1, supra. The effector activity was determined by contacting samples of 5000 CD8TLs with $2\times10^5$ HLA-A1 EBV-B cells which had been incubated for one hour with 1 µM of the peptide of SEQ ID NO: 1 at 37° C., and co-culturing the mixed sample, overnight. The amounts of IFN-γ and IL-2 resulting from the activation of the T cells were measured in the supernatants of the co-cultured cells via ELISAs.

It was observed that the CD8TLs produced IFNγ and IL-2 at day 0, with a significant drop at day 4. The ability to release IFN-γ was regained by day 14 (IL-2 levels were not measured).

In parallel, TCRβ intracellular LAT molecules, and CD3 zeta molecules were concentrated on the surface at the contact site with peptide-pulsed cells at day 0, but the CD8TLs failed to recruit these molecules at day 4

This pattern of loss, and then recovery of effector function, cytokine production and tetramer staining was observed with fifteen other CD8TL clones. The loss of tetramer binding followed by recovery was observed with CD8TL clone 5 as shown infra using tetramer concentrations ranging from 1 to 100 nM.

Example 4

The experiments described in this example show that the time course of recovery of high tetramer binding is influenced by the type of antigenic stimulation the CD8TLs receive.

CD8TL clone 5 is a second clone which recognizes complexes of SEQ ID NO: 1 and HLA-A1 and lyses cells presenting these complexes. It is one of the fifteen cell lines referred to supra.

Stimulation of this CD8TL clone was carried out in three different ways. One way was the stimulation with irradiated tumor cells, referred to supra for clone A10. A second approach was stimulation with 0.5 µg/ml of phytohemaglutinnin. A third method used $3\times10^5$ EBV-B cells that were HLA-A1 positive, and had been pulsed with peptide, as described, supra.

The same pattern, i.e., strong initial tetramer binding, followed by a drop, and recovery within about 2 weeks, was observed when the stimulus was peptide pulsed, tumor cells; however, stimulation with the EBV-B cells maintained the cells in a "tetramer$^{low}$" binding phenotype for 2 weeks, with "tetramer$^{high}$" binding only recovered after 4 weeks. The same results were obtained with PHA stimulation.

In additional studies, the effect of frequency of stimulation was tested, by stimulating the clone 5 cells, 4 times, at 3 day intervals. This maintained the CD8TLs in a "tetramer$^{low}$" phenotype for 2 weeks, with another 3 weeks being necessary to regain the high staining phenotype.

These data indicate that the duration of tetramer$^{low}$ phenotype is correlated to the strength, and duration, of antigenic stimulation.

Example 5

The reduced ability to bind tetramers following stimulation of long term CD8TLs suggested a further set of experiments, to determine if this phenomenon could be observed ex vivo, i.e. with lymphocytes collected from the body, as opposed to long term CD8TL clones.

Blood cells were obtained from a donor, and mononuclear cells were isolated via standard methods, after which they were cultured for 20 days, in complete IMDM medium with 50 U/ml of IL-2, and one of Epstein-Barr virus peptide GLCTLVAML (SEQ ID NO: 2), at 5 µM, or PHA (0.5 µg/ml), or an irrelevant peptide. The mononuclear cells were HLA-A2 positive, and SEQ ID NO: 2 is known to bind with HLA-A2.

Following the single stimulation, cells were stained with PE labeled tetramers, containing SEQ ID NO: 2, as described supra.

In the results which follow, it will be seen that during the first week, there was almost no tetramer staining, regardless of the stimulation; however, review of the results secured 20 days after stimulation shows that selective proliferation did in fact occur.

Example 6

As discussed supra T lymphocytes which express both CD8 and TCR molecules on their surface in normal amounts fail to engage and fail to bind HLA-peptide tetramers at one stage of their stimulation cycle. In view of this, studies were carried out to determine the distribution of these molecules on cell membranes of both "tetramer$^{high}$" and "tetramer$^{low}$" binding subpopulation of clone A10. To describe these subpopulations briefly, the "tetramer$^{high}$" subpopulation had not been contacted with antigen for 15 days, while the "tetramer$^{low}$" subpopulation had been contacted with peptide pulsed cells, 4 days before the study.

Cells were fixed to cover slips, and then stained with a combination of an anti-TCRβ antibody, and an "Alexa-568" coupled secondary antibody, which provides a red stain, and a second combination of an anti-CD8α antibody and a secondary, "Alexa488" coupled antibody, which provides a green stain. Standard assay conditions were used.

On most cells of the "tetramer$^{high}$" population, the molecules co-localized, appearing as a unique yellow ring. The "tetramer$^{low}$" subpopulation, CD8α molecules located on an outer ring on the equator, while TCRβ located on an inner ring, indicating segregation of the molecules.

Example 7

Given the apparent co-localization of the co-receptors on tetramer$^{high}$ cells, it was of interest to determine if they were close enough to cooperate with respect to tetramer binding. To determine this, "fluorescence resonance energy transfer" or "FRET" techniques were used.

To elaborate, samples of $2 \times 10^5$ cells were washed in Hank's medium that had been supplemented with 1% human serum, and were then resuspended, in 50 µl of medium, which contained either an anti-TCRβ-PE antibody (the "donor" antibody), or an anti-CD8α-Alexa647 antibody (the "acceptor" antibody), or both. The former was diluted at 1/20 and the latter, at 1/300.

Samples were incubated for 30 minutes at 4° C., washed, and fixed with paraformaldehyde (2% w/v in PBS). Analysis was carried out on a FACS system, and transfer of fluorescence was calculated as FRET units, in accordance with Doucey et al., *J. Biol. Chem.*, 278:3257-3264 (2003), incorporated by reference. A FRET unit is defined as:

$$[E3_{both}-E3_{none}]-[(E3_{A647}-E3_{none}) \times (E2_{both}/E2_{A647})]-[(E3_{PE}-3_{none}) \times (E1_{both}/E1_{PE})]$$

E1 is the fluorescence detected at 580 nm, following excitation at 488 nm. E2 is fluorescence detected at 670 nm, following excitation at 630 nm, and E3 is fluorescence detected at 670 nm following excitation at 488 nm.

After the molecules are excited at the donor level, transfer of energy from donor to acceptor happens only if the distance between two molecules is less than 10 nm, with energy transfer being measured by emission at the acceptor wavelength.

Substantial transfer of energy was observed only with the "tetramer$^{high}$" population shown that, on this subpopulation of CD8TLs, the CD8 and TCR molecules are, in fact, close enough to play their co-receptor role in binding HLA-peptide complexes.

Example 8

The results obtained in the prior examples suggest that CD8 molecules are segregated from TCR molecules, on the "tetramer$^{low}$" subpopulation of CD8TLs. This implies that some anchoring activity must cause this.

Previously, Foti, et al., *Proc. Natl. Acad. Sci. USA*, 99:2008-2013 (2002), showed that p56$^{lck}$ anchors CD4 in lipid rafts, localized on microvilli. The p56$^{lck}$ molecule has also been shown to bind CD8α. Barber, et al., *Proc. Natl. Acad. Sci. USA*, 86:3277-3281 (1989). It is also known that Zn is essential for both binding events. See, Lin, et al., *J. Biol. Chem.*, 273:32878-32882 (1998). It was thus proposed that if p56$^{lck}$ anchors CD8α at a distance away from TCR in the "tetramer$^{low}$" subpopulation, if CD8α molecules were released, a zinc chelator could in fact restore the proximity of the two relevant molecules and their ability to bind tetramers.

To test this, cells of CD8TL clone A10 were collected, on days 0 and 4, after stimulation with HLA-A1$^+$, MAGE-3$^+$ tumor cells. Mean fluorescence indices were determined for both the high and low staining populations, on days 0 and 4. FRET staining was carried out, as described supra, with cells that were either incubated with no test substance, or which had been incubated for 2 hours, on day 4, with one of o-phenantholin (30 µM), a known Zn chelator, lactose, (100 mM), LacNAc (1 mM), or sucrose (100 nM). The rationale behind the incubation with lactose, LacNAc, and sucrose is explained in Example 11. A final sample was incubated with swainsonin (0.5 µM) on day 0, before the cells were stimulated.

The cells were then washed, and analyzed for all of tetramer staining, proximity of the molecules via FRET, and IFN-γ production following antigenic stimulation.

It was indeed observed that when the "tetramer$^{low}$" subpopulation was treated with o-phenantholin, it regained FRET exchanges between the 2 molecules, the ability to bind tetramers, and the ability to release IFN-γ when stimulated with antigen.

Example 9

It has been proposed by, e.g., Demetriou, et al., *Nature*, 409:733-739 (2001), and Morgan, et al., *J. Immunol.*, 173:7200-7208 (2004), that N-glycosylated, TCR molecules could be part of a lattice formed by surface glycoproteins, with extracellular galectin-3. This trapping of the TCR in a lattice could be responsible for the anchoring of the TCR at a distance of the CD8.

Galectin-3 binds with high affinity to N-acetyl lactosamine ("LacNAc") motifs, which are located near the end of branched, sugar structures, that are bound to asparagine residues. Ahmad, et al., *J. Biol. Chem.*, 279:10841-10847 (2004) show that galectin-3 favors lattice formation, because it forms homopentamers. The relevant branched sugar structures are built via a series of enzymes in an N-glycosylation pathway and β1-6-N-acetylglucosaminyl transferase V ("MGAT5" hereafter), modifies branched structures to allow other enzymes to add the LacNAc motifs.

Example 10

In experiments which followed up on those described supra, FRET analysis was carried using one of (i) anti-TCRβ-PE or anti-galectin-3 PE (as donor), and one of (ii) anti-CD8β-Alexa 647, or anti-TCRβ-Alexa 647 (as acceptor) and as described supra. Following staining, cells were fixed and analyzed, via flow cytometry. Staining was carried out on cells at day 0, and 4 days after stimulation, and both the "tetramer$^{high}$" and "tetramer$^{low}$" subpopulations were tested.

Co-localization of galectin-3 and TCR were found on the "tetramer$^{low}$" subpopulation of CD8TLs, but not on the "tetramer$^{high}$" subpopulation. No proximity was found between CD8 and galectin-3 on either population.

Example 11

In the examples discussed supra, incubation of CD8TLs with lactose or LacNAc was described. These are both known, galectin-3 ligands, and it was thought that this incubation might serve to release LacNAc bearing surface proteins, such as TCRs, from the lattice structure.

The results indicated that, as compared to untreated cells of "tetramer$^{low}$" phenotype, the cells which had been treated with either lactose or LacNAc showed higher FRET efficiencies, which indicated that there was greater TCR-CD8 localization. They also showed higher degrees of tetramer staining, and a higher ability to release IFN-γ when subjected to antigenic stimulation.

Sucrose is not a galectin-3 binder, and treatment with it had no effect. Swainsonin is a known inhibitor of α-mannosidase II, which is also involved in the N-glycosylation pathway referred to supra. When it was added to CD8TL medium prior to restimulation, cells showed higher tetramer staining (at day 4), as well as higher FRET efficiency and a higher ability to release IFN-γ when restimulated.

Example 12

These experiments were designed to determine if TCRs and CD8 molecules colocalize on TILs. It has been reported that solid tumors in humans, as well as tumor ascites, are infiltrated by T cells. See, e.g., Ionnides, et al., *J. immunol.*, 146:1700-1707 (1991); Yannelli, et al., *Int. J Cancer*, 65:413-421 91996); Zorn, et al., *Eur. J. Immunol.*, 29:602-607 (1999). In the case of melanoma, detail studies revealed that most of these TILs are ineffective in situ, i.e., tumors clearly progress notwithstanding the presence of the TILs. See, Germeau, et al., *J. Exp. Med.*, 201:241-248 (2005); Lurquin, et al., *J. Exp. Med.*, 201:249-257 (2005). In studying TILs from solid tumors, since the nature of the HLA-peptide complexes was not known, tetramer staining was not a viable option; however, the FRET analysis described supra does provide a viable methodology for these experiments.

A standard depletion strategy was used to isolate CD8$^+$ T cells from a breast carcinoma metastasis, ovarian carcinoma ascites, blood, and a kidney allograft that had been resected during a chronic rejection process.

The breast and ovarian carcinoma ascites provided enough CD8$^+$ TILs to carry out the assay, and the FRET analysis of the TCR and CD8 proximity showed no significant transfer of energy between TCRs and CD8, showing a lack of colocalization. This was in strong contrast to CD8$^+$ T cells from blood, which showed a clear energy transfer. Energy transfer was also apparent with CD8$^+$ T cells isolated from the kidney allograft resection. The transfer was equivalent to that on control tetramer$^{high}$ CD8TL clones. The conclusion from this is that TIL anergy is associated with a lack of colocalization of TCR and CD8.

Example 13

The question that was then posed was whether the functions of CD8TLs could be restored by appropriate treatment.

These experiments tested the impact of N-acetyllactosamine (LacNAc) on colocalization. Gastric carcinoma ascites were screened for CD8$^+$ TILs, after they had been incubated for various time periods at 37° C., with 1 mM of LacNAc, and washed. As a control, the line CD8TL A10 was used, two weeks after its last antigenic stimulation. It was found that, after 5 hours of treatment with LacNAc, the TILs had recovered the same level of TCR CD8 FRET as had been observed on tetramer$^{high}$ CD8TLs.

Not surprisingly, when assays for IFN-γ were carried out with TILs from ovarian cancer ascites, the TILs did not produce IFN-γ even after overnight stimulation with a mixed population of tumor cells, B cells and macrophages (from the same ascites), or with allogenic, EBV-B cells. The TILs showed low responsiveness to CD3/CD28 stimulation; however, an overnight incubation with 1 mM LacNAc boosted IFN-γ response to antigen stimulation by more than 10 fold. This was also the case for release of TNF-α, IL-4, IL-5, and IL-10. Similar results were secured with ascites for endometrium carcinoma and ovarian carcinoma.

As was noted supra, there was clear TCR CD8 FRET on kidney infiltrating T cells isolated from the kidney allograft. These T cells released IFN-γ upon stimulation with allogeneic EBV-B cells, or beads coated with anti-CD3/CD28 antibodies. The LacNAc treatment did not result in increased IFN-γ production.

Example 14

The preceding experiments established that TCR and CD8 co-receptors are separated on tetramer$^{low}$ cells, and on TILs. This opened the possibility that they are anchored, at different locations on the cell membrane, by different molecules.

Demetriou, et al., *Nature*, 409:733-739 (2001), and Morgan, et al., *J. Immunol.*, 173:7200-7208 (2004), have suggested that N-glycosylated TCR molecules belong to a surface lattice of glycoproteins, clustered by extracellular galectin-3. It is known that galectin-3 binds, with high affinity, to LacNAc motifs, positioned near the end of N-linked branched sugar structures which are bound to asparagine residues of surface proteins. Lattice formation occurs as a result of homopentamers formed by galectin-3. (Ahmad, et al., *J. Biol. Chem.*, 279:10841-10847 (2004).

If one assumes a TCR molecule is anchored, in a glycoprotein-galectin-3 lattice, at a distance from a CD8 molecule, it might be the case that a galectin-3 ligand would release the TCR upon binding to galectin-3, thus restoring proximity of TCR and CD8, and the function of a T cell.

To test this, tetramer$^{low}$ CD8TLs, collected 3-4 days after stimulation, as described supra, were treated with LacNAc, a known competitive binder of galectin-3. Release of IFN-γ was restored.

These experiments were repeated testing two other galectin-3 binders, "tri-LacNAc," and an antibody against the N-terminus of galectin-3. Both of these substances exerted similar effects on the target CD8TLs.

Similarly, when cells were treated with neuraminidase, which is known to cleave sialic acid from many glycans, the effect was similar to that of LacNAc.

The experiments described herein, using neuraminidase, were carried out on human CD8TLs, and the results parallel those observed by Kao, et al., *Immunol.*, 17:1607-1617 (2005), on murine cells. It is hypothesized that a sialic acid residue may be present, near the LacNAc motif of galectin-binding proteins, and act to increase galectin-3 affinity.

Example 15

The experiments described supra, using FRET analysis, showed that there was a lack of colocalization in anergic CD8+ TILs isolated from tumors, while the clear energy transfer on CD8+ blood T cells indicated colocalization had occurred. These results lead to the conclusion that TIL anergy is in fact associated with a lack of receptor colocolization. It was confirmed by the fact that, notwithstanding overnight stimulation with a mixed population of tumor cells, B cells, and macrophages collected from the same ascites, or with allogenic EBV-β cells. IFNγ was not produced. They also exhibited a very low response to anti-CD3/CD28 stimulation.

When these anergic TILs were incubated overnight with 1 mM LacNAc, their IFN-γ response increased more than 10 fold. Similar results were obtained with TILs treated with TriLacNAc, and neuraminidase.

Different treatments were not, however, unspecific. Functional kidney infiltrating lymphocytes, and functional CD8TL 3.2, collected fifteen days post stimulation, did not show an increased ability to release IFN-γ, notwithstanding the treatment.

The foregoing disclosure sets forth various features of the invention, which relates to methods for modulating activity of a CD8 T lymphocyte ("CD8TL" hereafter, or "CD8TLs" when the plural is used), by increasing or decreasing it. "Increasing activity" as used herein, refers both to augmenting pre-existing activity of a CD8TL, even if that activity is at a low level, and to activating a CD8TL which is showing no activity. This is accomplished by contacting the CD8TL with a substance that enables two components necessary for T lymphocyte activity, i.e., the CD8TL receptor and co-receptor, to change the distance between each other. If the modulator that is used is an activating agent, it reduces the distance between the receptor and the co-receptor such that they interact in a fashion characteristic of active and functional T lymphocytes, and vice versa for an inhibiting agent. Conversely, "decreasing activity" refers to lowering pre-existing activity of a T lymphocyte, or even eliminating it. Activity is also the production of cytokines such as IFN-gamma.

The co-receptors are CD8 molecules and the receptors are T cell receptor molecules. The method involves contact with one or more substances which release one or both molecules from lattices to which they are bound or strengthen that interaction.

The nature of these "modulators" will vary, as the nature of lattice binding or anchoring to the cell membrane differs for each receptor and co-receptor, and explained supra. For example, a zinc chelator, such as o-phentholin can be used to release a CD8 molecule from the cell membrane which it is anchored. N-glycosylation pathway inhibitors, such as β1-6-N-acetylglucosaminyl transferase inhibitors, e.g., swainsonin, may be used to impede the formation of the TCR-galectin lattice. When release of the T cell receptor from the lattice is desired, a galectin ligand, such as a galectin-3 ligand, e.g., lactose, or an oligosaccharide which comprises an N-acetyl lactosamine motif, such as N-acetyl lactosamine molecule per se can be used.

It should be noted that the materials discussed supra are exemplary, but are not the only examples of substances which will accomplish the stated purpose of the invention, which is the modulation of activity of a CD8TL. Determining such modulation is easily determinable by one of ordinary skill in the art.

Exemplary of galectin-3 modulating molecules include GCS-100, a modified form of citrus pectin, described, e.g., by Chaunan, et al., *Canc. Res.*, 65(18):8350-8358 (2005), incorporated by reference. Published U.S. Patent application 2004/0223971, also incorporated by reference, describes modified pectins and carbohydrate containing polymers as inhibitors, as well as antibodies against galectin-3. U.S. Pat. No. 7,230,096, also incorporated by reference, also discusses carbohydrate derivatives as galectin-3 inhibitors. U.S. Pat. No. 6,770,622, cited supra and incorporated by reference, describes truncated forms of galectin-3, showing that proteins and polypeptides can serve as inhibitors of galectin-3 as well. Additional galectin-3 inhibitors embraced by the invention are described in U.S. Pat. No. 6,680,306, incorporated by reference, which teaches polymers with side chains that terminate with galectose and/or arabinose units.

All of these materials, as well as those described in the Examples, and substances which function in accordance with the definition of modulator set forth supra constitute a part of the claimed invention.

When increasing the activity of a T lymphocyte, the CD8TL is preferably one which is specific for a complex of an MHC molecule and a peptide associated with cancer, however, as CD8TLs target various peptide/MHC complexes, any CD8TL can be used, regardless of its specificity. While exemplification is provided for CD8 T lymphocytes, it is envisioned that the methodology is applicable to CD4 lymphocytes as well.

As noted supra, the disclosure provides various ways to determine if a compound or substance increases the activity of a CD8TL, and this screening assay feature is also a part of the invention. FRET analysis, as described supra, is especially preferred for this aspect of the invention.

Also a feature of the invention are what will be referred to as "combination therapies" and compositions that are useful in these. "Combination therapy" as used herein, refers to the use of a galectin-3 modulator in combination with one or more peptides which are presented by MHC molecules and provoke an immune response, and/or a substance or combination of substances which undergoes processing to such a peptide. These peptides can be, e.g., tumor rejection antigen or T lymphocyte peptides, such as, but not being limited to, MAGE, BAGE, GAGE, NY-ESO-1, PRAME, FRAME, Melan-A, or other tumor rejection precursor based antigens, as well as other peptides known to be presented by MHC molecules on the abnormal cells of the patient being treated. It is well within the skill of the artisan to determine MHC type of a patient and to choose appropriate peptide. While so-called "Class I" binding peptides are preferred, Class II binding peptides may also be used, as well as combinations. While one or more peptides may be combined with the modulator, the modulator may also be combined with full length proteins, such as a so called "tumor rejection antigen precursor," as described supra, or some other material which functions as a vaccine. By vaccine is meant, e.g., a substance or combination of substance with the immune stimulating effect described supra. Non exhaustive exemplification of such vaccine materials include full length TRAPS, as described above, as well as fragments thereof, which are larger than the TRAs, and smaller than full length TRAPS, which are processed to one or more TRAs, isolated cells which present the TRA molecules on their surfaces, mutated viruses which express the protein in question, but have been modified to be harmless to the host, including etiolated forms of viruses, transfected bacteria which have been treated and rendered non-proliferative, and complexes of TRAs and an MHC or HLA molecule. These vaccine materials may be combined with an appropriate adjuvant. These are well known to the skilled artisan, and need not be repeated here.

In use, the therapeutic method may involve simultaneous use of the modulator and at least one peptide or other vaccine material as well as methods where the modulator precedes, or follows the at least one peptide or other vaccine material.

Compositions which are useful in these therapies are also a part of the invention. In combination therapy, the composition may include both the galectin-3 modulator and at least one peptide and/or vaccine material, together with a pharmaceutically acceptable carrier, which may be, e.g., an adjuvant. The composition may also include optional ingredients, such as a molecule which facilitates delivery of the inhibitor to the cells.

These compositions may also take the form of multi-component "kits," where separate portions of the modulator and the at least one peptide or other vaccine material are provided, in the form of pharmaceutically acceptable compositions, which are in turn presented in a kit type container, so that the treating physician, e.g., can inoculate, or otherwise administer one, then the other agent.

Any form of administration of the compositions is a part of the invention including, but not being limited to, intravenous, subcutaneous, controlled delivery, oral, intramuscular, sub venous, and other forms of therapy known to one of skill in the art.

Other features of the invention will be clear to the skilled artisan, and need not be set forth here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

What is claimed is:

1. A method for increasing activity of a T lymphocyte consisting of contacting said T lymphocyte with a composition consisting of a galectin-3 ligand and a carrier, in an amount sufficient to reduce distance between a T cell receptor and a T lymphocyte co-receptor to a point sufficient to increase activity of said T lymphocyte, said contacting occurring in vitro.

2. The method of claim 1, wherein said T lymphocyte has a low level of T cell activity.

3. The method of claim 1, wherein said T lymphocyte is a CD8 cell.

4. The method of claim 1, wherein said T lymphocyte is a CD4 cell.

5. The method of claim 1, wherein said T lymphocyte co-receptor is a CD8 molecule.

6. The method of claim 1, wherein said galectin-3 ligand is lactose.

7. The method of claim 1, wherein said galectin-3 ligand is an oligosaccharide which comprises an N-acetyl lactosamine motif.

8. The method of claim 7, wherein said oligosaccharide is N-acetyl lactosamine.

9. The method of claim 1, wherein said T lymphocyte is specific for a complex of an MHC molecule and an associated peptide.

10. The method of claim 1, wherein increasing activity comprises releasing said T cell receptor from a lattice of which it is a part via contact with said galectin-3 ligand.

11. The method of claim 1, wherein said activity is IFN-γ production.

12. The method of claim 1, wherein said activity is production of at least one of TNF-α, IL-4, IL-5, and IL-10.

13. The method of claim 1, wherein said galectin-3 ligand is an anti-galectin-3 antibody which binds to the N-terminus of galectin-3.

14. The method of claim 9, wherein said associated peptide is a cancer associated peptide.

* * * * *

SEQUENCE LISTING

```
<160> NUMBER OF SEQ ID NOS: 2

<210> SEQ ID NO 1
<211> LENGTH: 9
<212> TYPE: PRT
<213> ORGANISM: homo sapiens
<220> FEATURE:

<400> SEQUENCE: 1

Glu Val Asp Pro Ile Gly His Leu Tyr
1               5

<210> SEQ ID NO 2
<211> LENGTH: 9
<212> TYPE: PRT
<213> ORGANISM: Homo sapiens
<220> FEATURE:

<400> SEQUENCE: 2

Gly Leu Cys Thr Leu Val Ala Met Leu
1               5
```